(12) United States Patent
Heremans et al.

(10) Patent No.: US 6,911,830 B2
(45) Date of Patent: Jun. 28, 2005

(54) DIESEL ENGINE LUBRICATING OIL CONTAMINANT SENSOR METHOD

(75) Inventors: Joseph Pierre Heremans, Troy, MI (US); Su-Chee Simon Wang, Troy, MI (US); Thaddeus Schroeder, Rochester Hills, MI (US); Louis L. Nagy, Warren, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/226,100

(22) Filed: Aug. 22, 2002

(65) Prior Publication Data

US 2004/0036487 A1 Feb. 26, 2004

(51) Int. Cl.[7] .............................................. G01R 27/08
(52) U.S. Cl. ...................... 324/698; 327/439; 327/441; 327/633; 73/53.05; 702/50
(58) Field of Search ................................. 324/698, 658, 324/439, 441; 73/35.02, 53.01, 53.05, 53.06; 702/50

(56) References Cited

U.S. PATENT DOCUMENTS

| | | | |
|---|---|---|---|
| 4,112,744 A | 9/1978 | Tassano | 73/61.1 R |
| 4,281,533 A | 8/1981 | Eesley et al. | 73/15 R |
| 4,345,202 A | 8/1982 | Nagy et al. | 324/58.5 B |
| 4,503,384 A | 3/1985 | Nagy et al. | 324/61 P |
| 4,646,070 A | 2/1987 | Yasuhara et al. | 340/603 |
| 4,733,556 A | 3/1988 | Meitzler et al. | 73/64 |
| 5,604,441 A | 2/1997 | Freese, V et al. | 324/663 |
| 5,656,767 A | 8/1997 | Garvey, III et al. | 73/61.44 |
| 5,824,889 A | 10/1998 | Park et al. | 73/116 |
| 5,933,016 A * | 8/1999 | Kauffman et al. | 324/698 |
| 5,973,503 A * | 10/1999 | Kuipers et al. | 324/698 |
| 6,278,282 B1 * | 8/2001 | Marszalek | 324/663 |
| 6,509,749 B1 | 1/2003 | Buelna et al. | 324/698 |
| 6,535,001 B1 | 3/2003 | Wang | 324/698 |
| 6,557,396 B2 | 5/2003 | Ismail et al. | 73/53.05 |
| 6,575,018 B2 | 6/2003 | Berndorfer et al. | 73/54.01 |
| 6,590,402 B2 | 7/2003 | Wang et al. | 324/698 |

OTHER PUBLICATIONS

"Standard Test Method for Evaluation of Diesel Engine Oils in T–8 Diesel Engine," ASTM, Designation: D 5967–99, An American National Standard, Aug. 1999.

Ian White et al, "Effect of Bulk Electrical Conductivity on TDR Measurement of Water Content in Porous Media," Symposium and Workshop on Time Domain Reflectometry in Environmental, Infrastructure, and Mining Applications held at Northwestern University, Evanston, Illnois, Sep. 17–19, 1994 (Washington DC: US Bureau of Mines, 1994), pp 294–308.

George S. Saloka et al, "A Capacitive Oil Deterioration Sensor," Electronic Materials and Devices Dept., Ford Motor Co., SAE No. 910497.

Eckard Irion et al, "Oil–Quality Prediction and Oil–Level Detection with the TEMIC QLT–Sensor Leads to Variable Maintenance Intervals," SAE No. 970847, 1997.

Peter E.M. Frere et al, "An On–Line Oil Viscosity Sensor," SAE No. 970848, 1997.

Generic oil condition sensor, on the market since at least Jan. 1, 2001.

* cited by examiner

Primary Examiner—N. Le
Assistant Examiner—Vincent Q Nguyen
(74) Attorney, Agent, or Firm—Jimmy L. Funke

(57) ABSTRACT

A method by which contaminant (soot) content in Diesel engine oil is determined using electrical conductivity measurements of the Diesel oil at a high frequency, or by which contaminant (soot and/or water and/or anitfreeze) content is determined using the ratio of electrical conductivity measurements of the Diesel oil at a high frequency to the electrical conductivity measurements of the Diesel oil at a low frequency. Both the conductivity ratio and the high frequency conductivity are essentially independent of the brand of oil. High frequency is defined to be above 2 MHz whereas low frequency is defined to be D.C. to about 1 kHz.

15 Claims, 15 Drawing Sheets

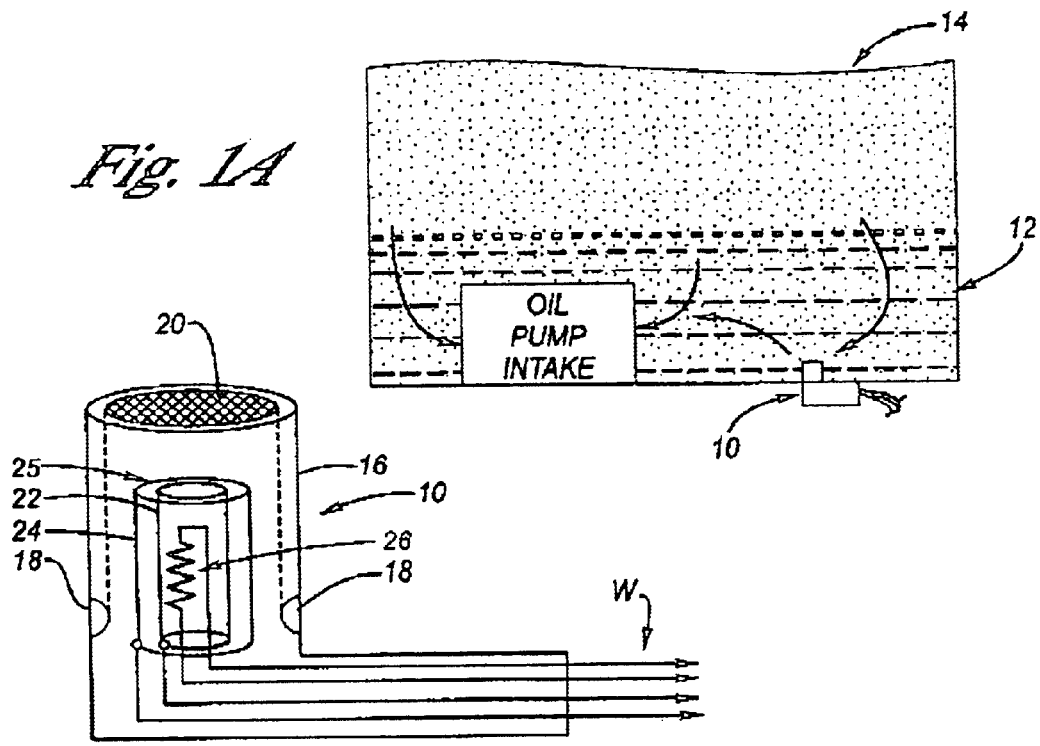
Fig. 1A
Fig. 1B
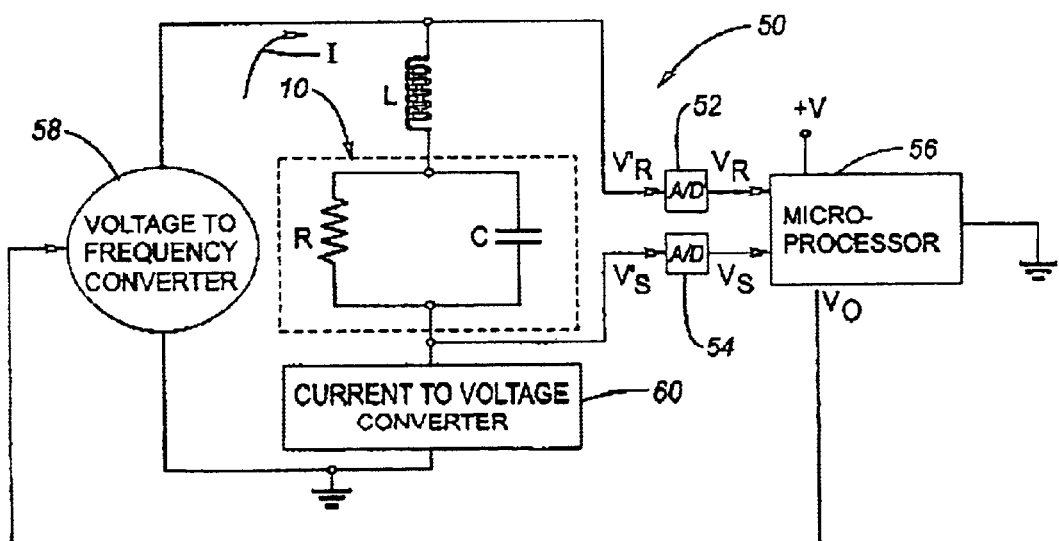
Fig. 2A

DIESEL ENGINE LUBRICATING OIL CONTAMINANT SENSOR METHOD

TECHNICAL FIELD

The present invention relates generally to Diesel engine oil contaminant sensors and more specifically to a method that measures the electrical conductivity of the lubricating oil to determine the amount of at least one of soot, water and antifreeze therein.

BACKGROUND OF THE INVENTION

Lubricating oil used in gasoline engines for lubrication of moving components, hereinafter simply referred to as "oil", deteriorates by the depletion of the additives and the increase in the acidity of the oil, as measured by a quantity called the total acid number (TAN). Oil in Diesel engines is degraded by the same mechanisms as in gasoline engines, but with the additional presence of soot particles, which increases as the oil ages. During usage of a Diesel engine, the crankcase oil gradually builds up soot which is a combustion product in the combustion chamber of the engine and which is transferred in small amounts to the crankcase oil. When the soot builds up to an unacceptable amount, say about four percent by mass or weight of the oil, the lubricating quality of the oil is inhibited. Thus, it is necessary to change the crankcase oil whenever the soot content reaches an unacceptable value. For this purpose, it is desirable to measure the soot content in the crankcase oil in order to detect the presence of an unacceptable percentage of soot.

Many different methods or techniques have been proposed for the measurement of soot in Diesel engine oil. In order to make the soot measurement on operating vehicles, it is necessary to provide a measuring system which is sufficiently inexpensive to incorporate on automotive vehicles made in large numbers and sufficiently rugged to withstand the Diesel engine operating environment. Moreover, a method of measuring soot in crankcase oil must be valid for many types of oil, both natural and synthetic, and containing many different types of additives.

U.S. Pat. Nos. 5,824,889; 5,656,767; and 4,733,556, and the Society of Automotive Engineers technical papers 970847 and 910497 describe how the dielectric constant (permittivity) can be used to describe the condition of Diesel oil or to detect the presence of moisture and antifreeze. The dielectric constant varies with the total acid number as well as the soot concentration; however, the variation in the dielectric constant between fresh oil and contaminated oil is not great. Furthermore, the dielectric constant of oil is also influenced by the temperature of the oil, by the specific formulation of a given brand of oil due to the additives that are deliberately added to the oil, by antifreeze, and by water.

The prior art describes a number of techniques that measure the dielectric constant with a sensor built like a capacitor. The capacitor like sensor includes two metal electrodes with the lubricating oil acting as the dielectric between the electrodes. The two metal electrodes take the form of two parallel plates or two concentric cylinders. Most of these sensors determine the permittivity of the oil through a measurement of the capacitance between the metal electrodes.

Sensors that measure the loss tangent, essentially the ratio of the electrical conductivity of the oil to the dielectric constant, have also been proposed. These sensors assume that the dielectric losses can be described by a single relaxation method, which is an inapplicable assumption, as used oil contains conductive particles (soot), polar molecules (water or antifreeze), and charged particles (ions). The presence of polar compounds increases the dielectric constant and affects the loss tangent making the loss tangent more sensitive to parasitic signals, such as the brand of oil or the presence of water and antifreeze. Delphi Automotive Systems has shown experimentally that such a sensor works only for selected oils due to the dependence of the measurement on the dielectric constant.

Delphi Automotive Systems also possesses a design for a gasoline engine oil contaminant sensor that measures the electrical conductivity of the oil using D.C. or a low frequency (below 1 kHz). The sensor consists of two metal electrodes, which can be parallel plates or concentric cylinders or rings. The conductivity is determined through a measurement of the electrical resistance between the electrodes. This sensor mainly detects the changes in the concentration of ions in the oil. In this regard, fresh oil is slightly basic. As the oil ages, the combustion products create acidic ions in the oil. At first, the acids neutralize the bases and the conductivity decreases. As the oil ages further, the increase in acidic ions makes the conductivity rise again. This makes for a very good oil quality sensor in gasoline engines. However, the soot in Diesel engine oils masks the ion density changes and renders this type of sensor useless.

Accordingly, what is needed in the art is a more robust method of detecting soot in Diesel engine oils, which is independent of the brand of oil and immune to the effects of adding fresh oil with different dielectric or electrical properties than the original oil.

SUMMARY OF THE INVENTION

The change in the dielectric constant of the oil (permittivity) is a relatively unreliable predictor of oil quality, because permittivity is greatly affected by presence of polar molecules, such as antifreeze, water and many of the additives that are deliberately added to engine oil. However, electrical conductivity at high frequencies (above 2 MHz) is extremely sensitive to the presence of soot, whereas the conductivity at low frequency (from D.C. to 1 kHz) is mostly sensitive to the presence of ions.

The present invention is a method by which soot content in Diesel engine oil is determined using electrical conductivity measurements of the Diesel oil at a high frequency, or using the ratio of electrical conductivity measurements of the Diesel oil at a high frequency to the electrical conductivity measurements of the Diesel oil at a low frequency which is independent of the brand of oil and immune to the effects of adding fresh oil with different dielectric or electrical properties than the original oil. High frequency is defined to be above 2 MHz (for example, up to about 10 GHz) whereas low frequency is defined to be D.C. to about 1 kHz.

Accordingly, it is one object of the present invention to measure the electrical conductivity of Diesel engine oil at a high frequency to determine the amount of soot therein which is independent of the brand of oil and immune to the effects of adding fresh oil with different dielectric or electrical properties than the original oil.

It is a second object of the present invention to measure the electrical conductivity of Diesel engine oil at a high frequency and the electrical conductivity of Diesel engine oil at a low frequency to determine the ratio of the electrical conductivity of Diesel engine oil at the high frequency to the electrical conductivity of Diesel engine oil at the low frequency thereby determining the amount of soot therein which is independent of the brand of oil and immune to the effects of adding fresh oil with different dielectric or electrical properties than the original oil. Herein, the ratio of the electrical conductivity of Diesel engine oil at the high frequency to the electrical conductivity of Diesel engine oil at the low frequency is referred to as the conductivity ratio.

These and additional objects, features and advantages of the present invention will become clearer from the following specification of a preferred embodiment.

BRIEF DESCRIPTION OF THE DRAWINGS

FIG. 1A depicts the engine placement of an oil sensor for conductivity measurements according to the present invention.

FIG. 1B depicts the oil sensor of FIG. 1 according to the Prior Art.

FIG. 2A is a first example of an electrical circuit to measure conductivity of Diesel oil at high frequencies.

DESCRIPTION OF THE PREFERRED EMBODIMENT

Figure 2B:
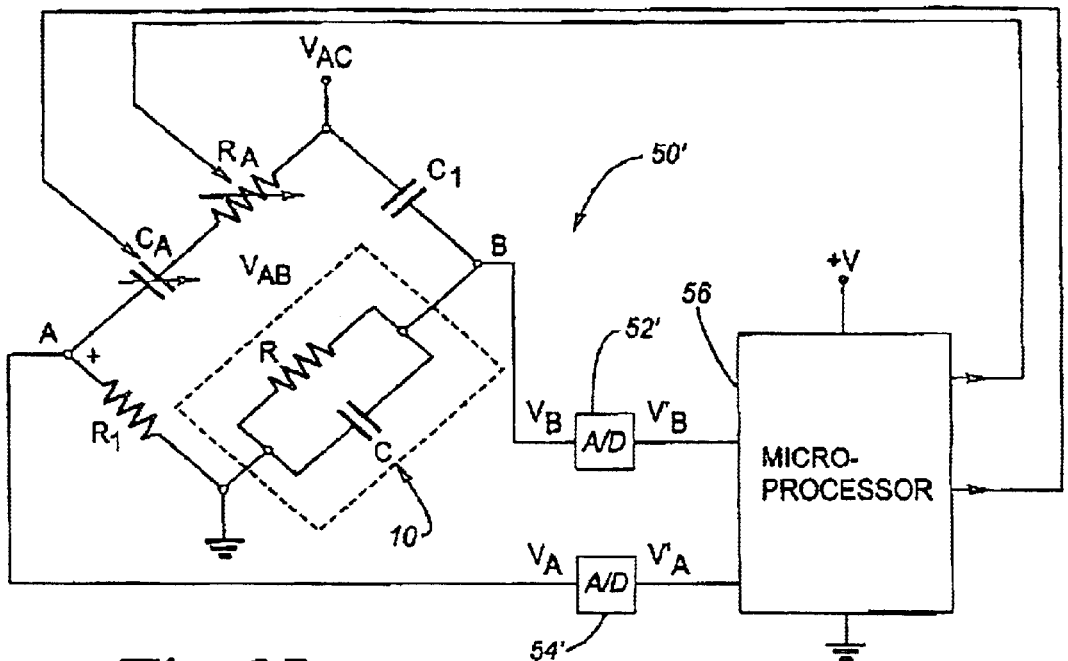
FIG. 2B is a second example of an electrical circuit to measure conductivity of Diesel oil at high frequencies.

Referring now to the Drawing, FIGS. 1A through 2C and 27 and 28 depict an example of apparatus to carryout the Diesel engine oil contaminant sensor method according to the present invention; and FIGS. 3 through 26 depict various graphical plots which support carrying out the various steps of the Diesel engine oil contaminant sensor method according to the present invention.

FIG. 1A depicts an environment of placement and operation of an oil sensor 10 at the bottom of an oil pan 12 of a Diesel engine 14. As shown at FIG. 1B, the oil sensor 10 has a cylindrical shell 16 having apertures 18 and an open top end 20. Inside the shell 16 is a pair of concentrically arranged and mutually separated cylindrical capacitor plates 22, 24 which collectively form a capacitor 25, each of which being connected to a respective portion of wiring, W. Depending on the method used according to the present invention, a thermometric sensor 26, as for example a thermistor, is placed within the shell and also connected to a respective portion of the wiring W.

In operation of the oil sensor 10, which sensor construction is known in the prior art, oil in the oil pan is sloshed and enters into the space separating the plates 22, 24, causing the capacitance C and the resistance R (see FIG. 2) of the space between the plates to change as the condition of the oil changes with hours of operation of the Diesel engine.

Figure 2C:
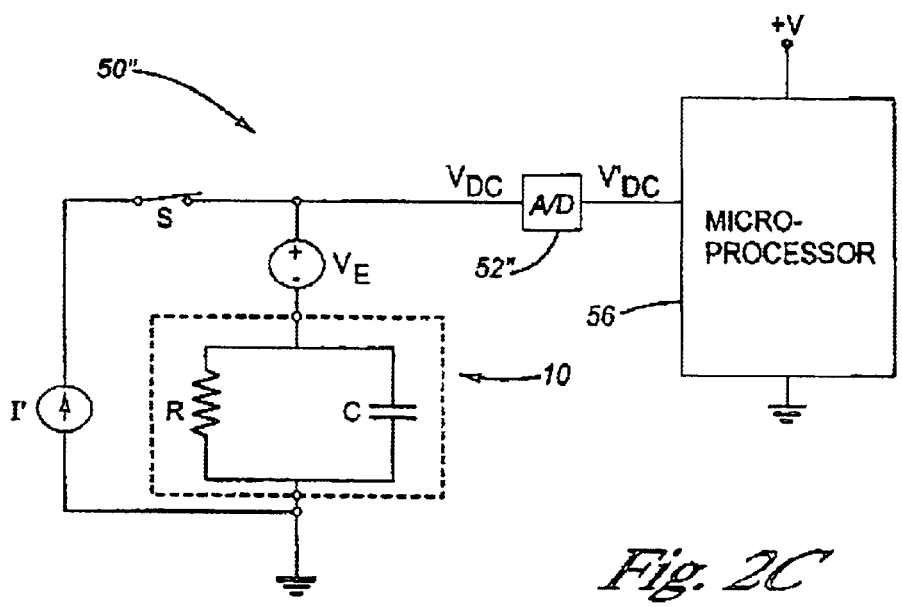
FIG. 2C is an example of an electrical circuit to measure conductivity of Diesel oil at D.C or low frequencies.

FIGS. 2A, and 2B are examples of electrical circuits to measure the conductivity of the Diesel oil at high frequencies whereas FIG. 2C is an example of an electrical circuit to measure the conductivity of Diesel oil at D.C. or low frequencies (i.e. 20 Hz). The operation of the circuits will be described hereinbelow after a description of the method hereof has been detailed.

A brief description of the various graphical plots will now be detailed in a progressive order which will incrementally describe the underlying principles of the method according to the present invention.

Figure 3:
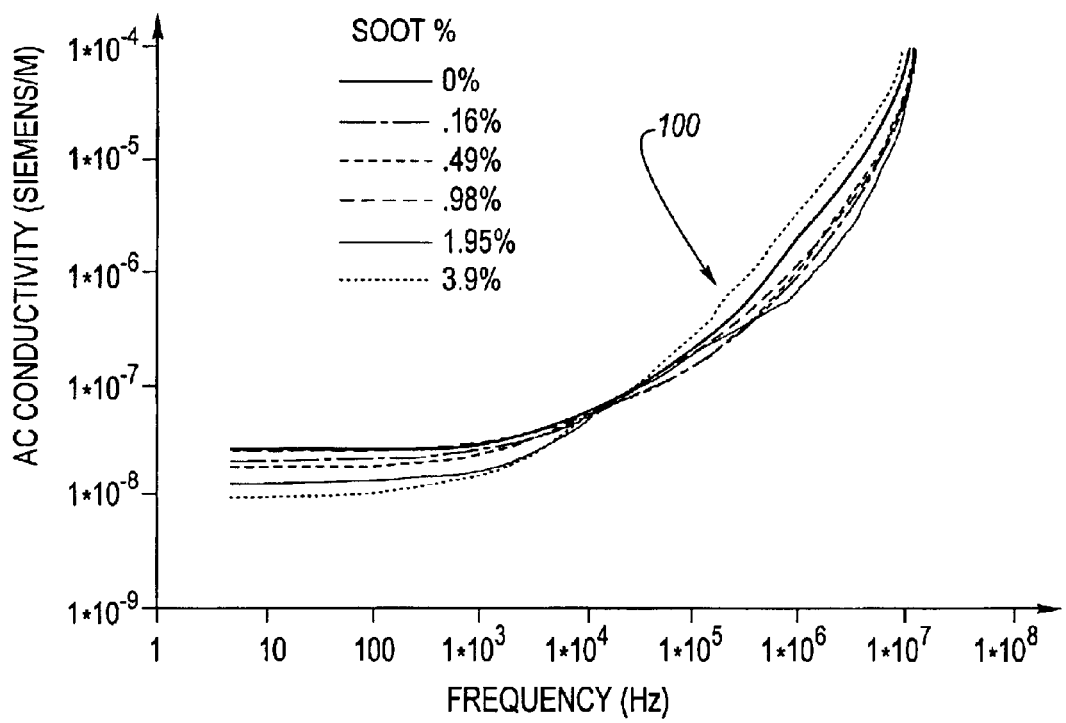
FIG. 3 is a plot of conductivity versus frequency of a first brand of fresh oil variously mixed with the same brand of used oil.

FIG. 3 is a plot 100 of conductivity versus frequency of a first brand of fresh oil variously mixed with the same brand of used oil. Fresh Rotella 15W40 Diesel engine oil was mixed with the same brand used in a Diesel engine in different ratios to simulate the condition of partially used oil. The used oil from the Diesel engine was analyzed to have a total acid number (TAN) of 5.1 mg KOH/mg sample and a soot concentration of 3.9% as measured by thermogravimetric analysis (TGA).

Figure 4:
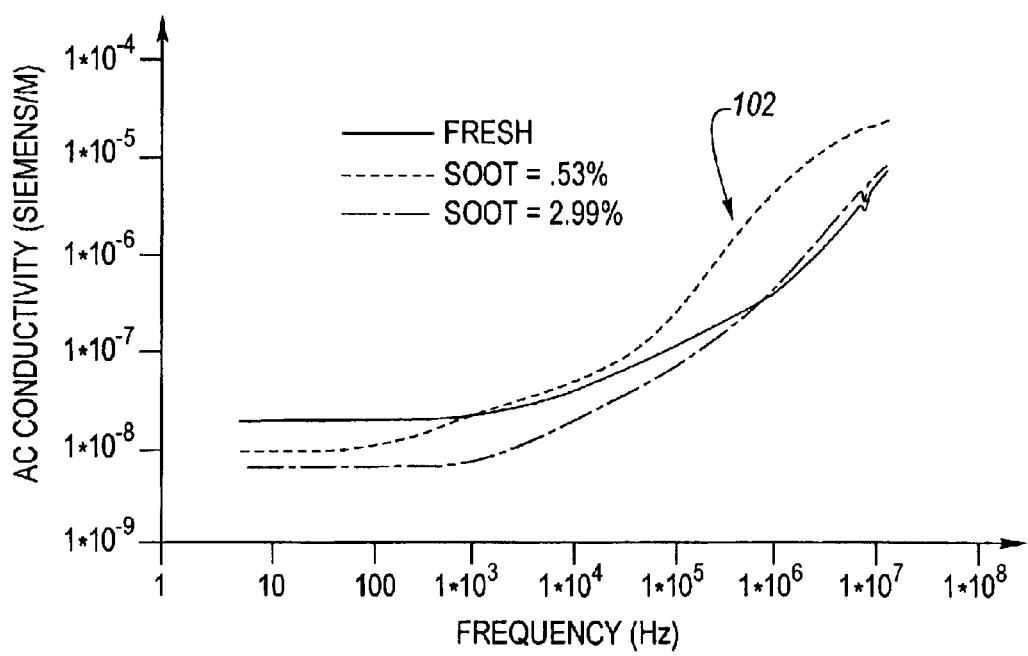
FIG. 4 is a plot of conductivity versus frequency of a second brand of aged oil.
Figure 5:
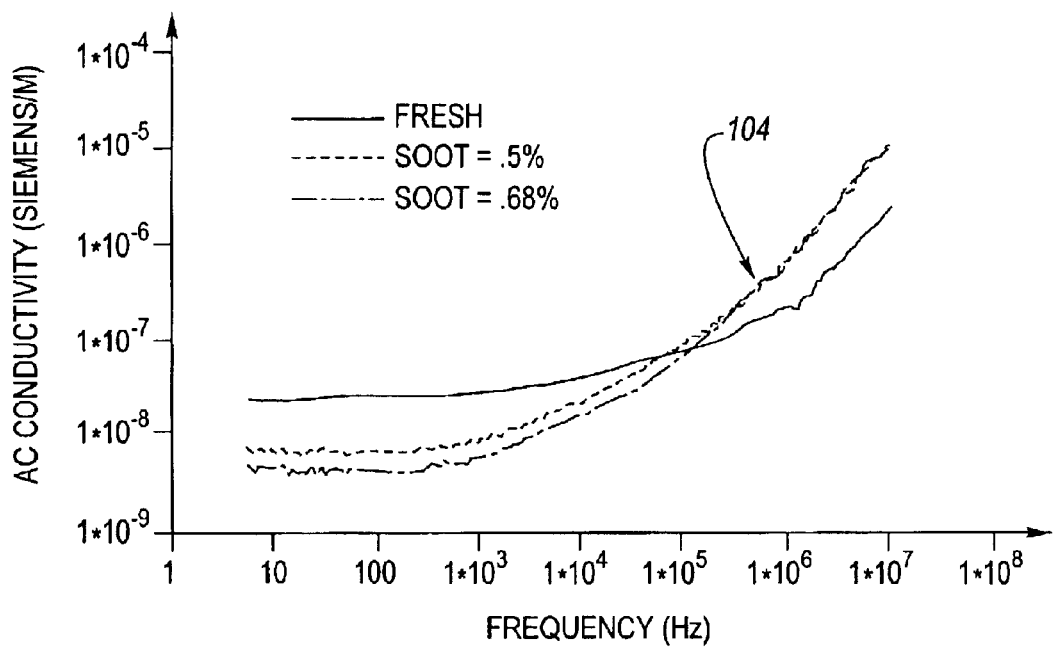
FIG. 5 is a plot of conductivity versus frequency of a third brand of aged oil.

FIG. 4 is a plot 102 of conductivity versus frequency of a second brand of aged oil while FIG. 5 is a plot 104 of conductivity versus frequency of a third brand of aged oil.

These two brands of Diesel engine oil were run in different engines and were used to access the influence of additions of fresh oil between oil changes.

Table 1 is a summary of the two oils used in FIGS. 4 and 5 and the aging they underwent. The oils were analyzed for total acid number (TAN), total base number (TBN), viscosity, and soot content as measured by thermogravimetric analysis (TGA).

Figure 8:
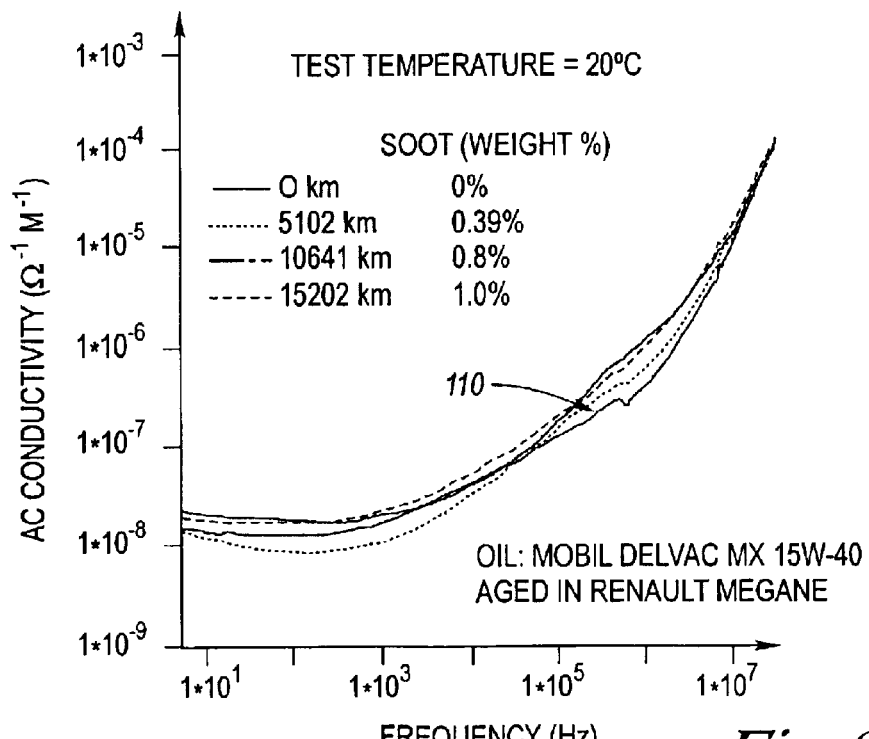
FIG. 8 is a plot of conductivity versus frequency of oil aged in a first vehicle.
Figure 9:
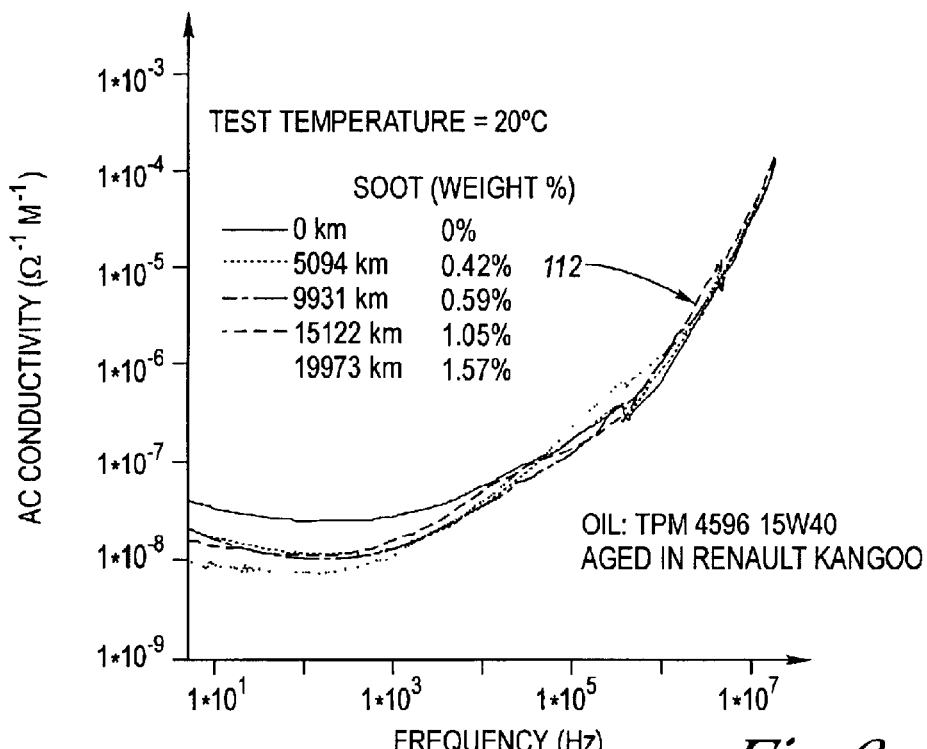
FIG. 9 is a plot of conductivity versus frequency of oil aged in a second vehicle.
Figure 10:
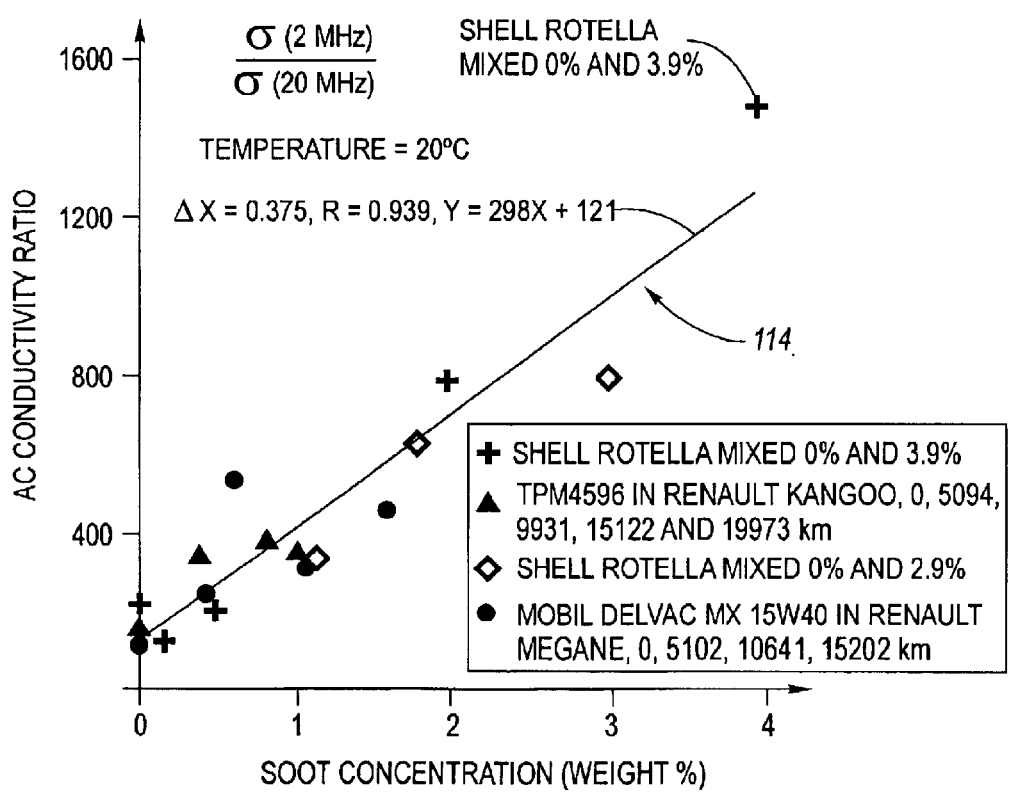
FIG. 10 is a plot of conductivity ratio versus soot concentration at a first temperature of the oils of FIGS. 3, 4, 8 and 9.
Figure 11:
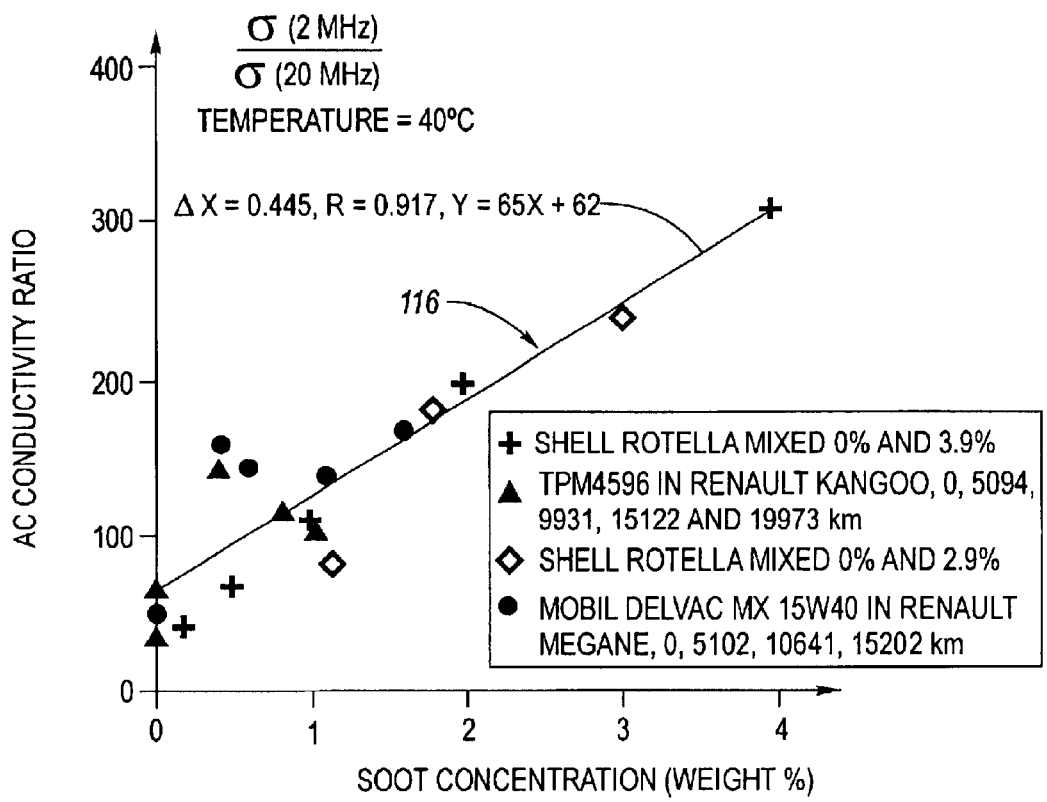
FIG. 11 is a plot of conductivity ratio versus soot concentration at a second temperature of the oils of FIGS. 3, 4, 8 and 9.

FIGS. 10 and 11 demonstrate that the method is brand independent and is correlated to soot content as well as showing that mixed oils have the same correlation as the oils of FIGS. 8 and 9. FIGS. 10 and 11, however, show that there is a temperature dependence to the ratio method.

Figure 12:
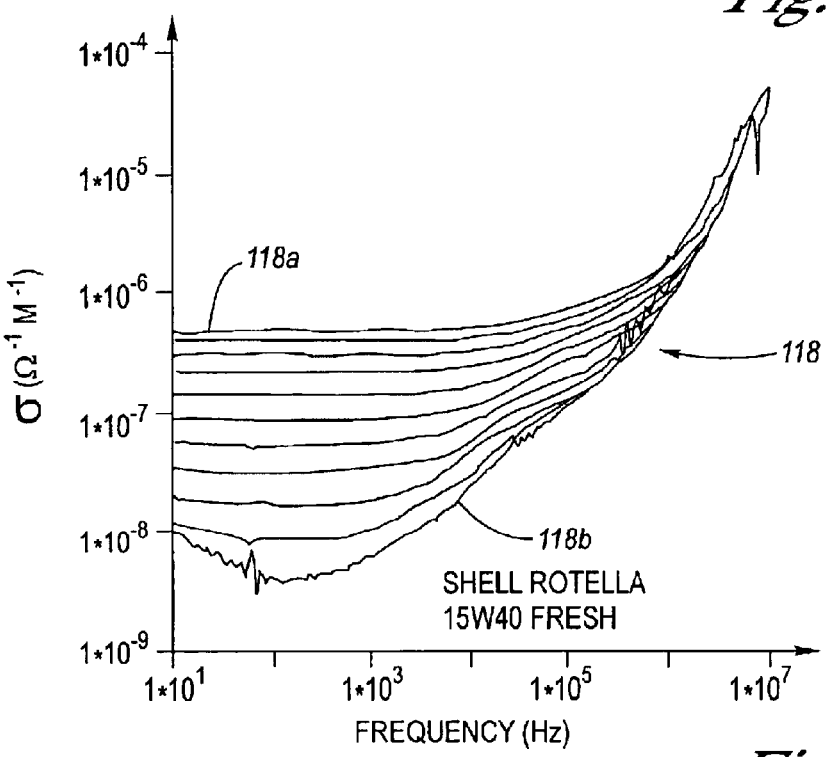
FIG. 12 is a plot of conductivity versus frequency of the fresh first brand of oil at various temperatures.

FIG. 12 is a plot 118 of conductivity versus frequency of the fresh first brand of oil at various temperatures from 100 degrees C. for plot 118a through decrements of 10 degrees

TABLE 1

| Sample | Oil | Car | TAN (mg KOH per g) | TBN (mg KOH per g) | Viscosity 40EC (cStokes) | Viscosity 100EC (cStokes) | Soot (TGA %) |
|---|---|---|---|---|---|---|---|
| Rotella | Shell Rotella T SAE 15W40 | VW Jetta | 0 | | | | 0 (initial) |
| 009 | Shell Rotella T SAE 15W40 | VW Jetta | 2.71 | 8.09 | 120.4 | 15.9 | 0.53 |
| 556 | Shell Rotella T SAE 15W40 | Dodge RAM | 12.14 | 3.66 | 186.4 | 21.7 | 2.99 |
| 077 | Texaco Ursa Sup Plus SAE 15E40 | Dodge RAM | 1.19 | 8.87 | 106 | 14.4 | 0 (initial) |
| 102 | Texaco Ursa Sup Plus SAE 15E40 | Dodge RAM | 2.25 | 8.38 | 103.7 | 13.9 | 0.5 |
| 361 | Texaco Ursa Sup Plus SAE 15E40 | Dodge RAM | 4.07 | 8.24 | 104.4 | 14.2 | 0.68 |
| 580 | Texaco Ursa Sup Plus SAE 15E40 | Dodge RAM | 4.11 | 7.92 | 117.1 | 14.8 | 0.83 |

Figure 6:
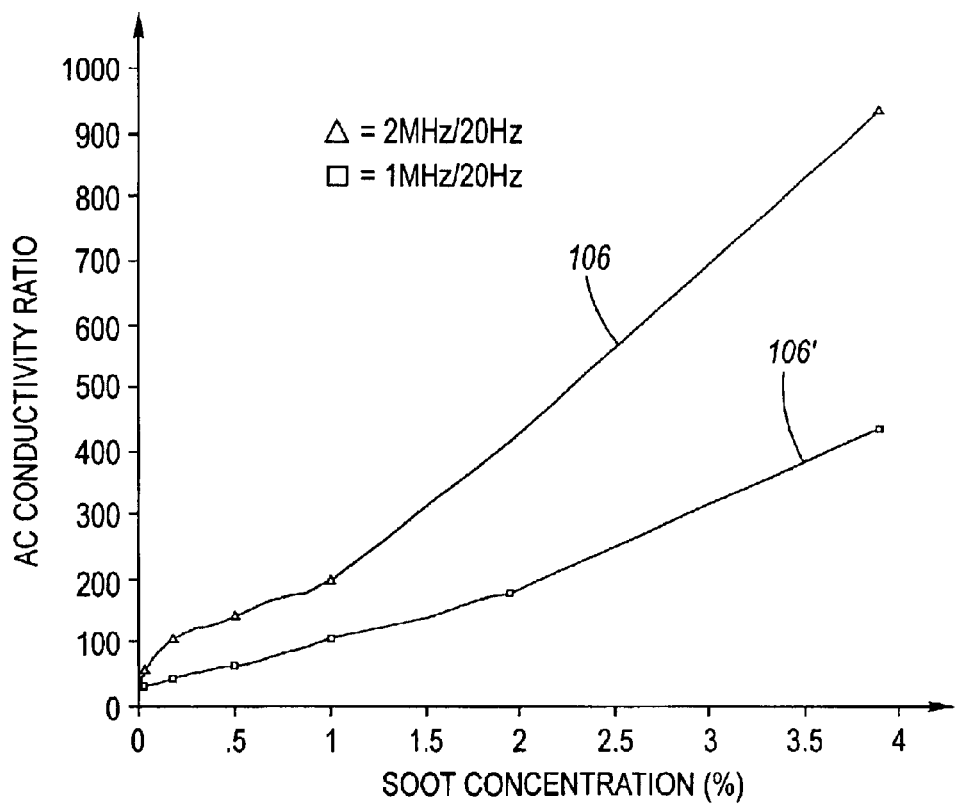
FIG. 6 is a plot of two conductivity ratios versus soot concentration of the oils of FIG. 3.

FIG. 6 shows plots 106, 106' of two conductivity ratios versus soot concentration of the oils of FIG. 3 at room temperature, wherein the conductivity ratios are, for plot 106, the conductivity measured at 2 MHz divided by the conductivity measured at 20 Hz, and for plot 106', the conductivity measured at 1 MHz divided by the conductivity measured at 20 Hz. Plots 106, 106' show the linearity of the method and the increased sensitivity for the ratio using the higher frequency.

Figure 7:
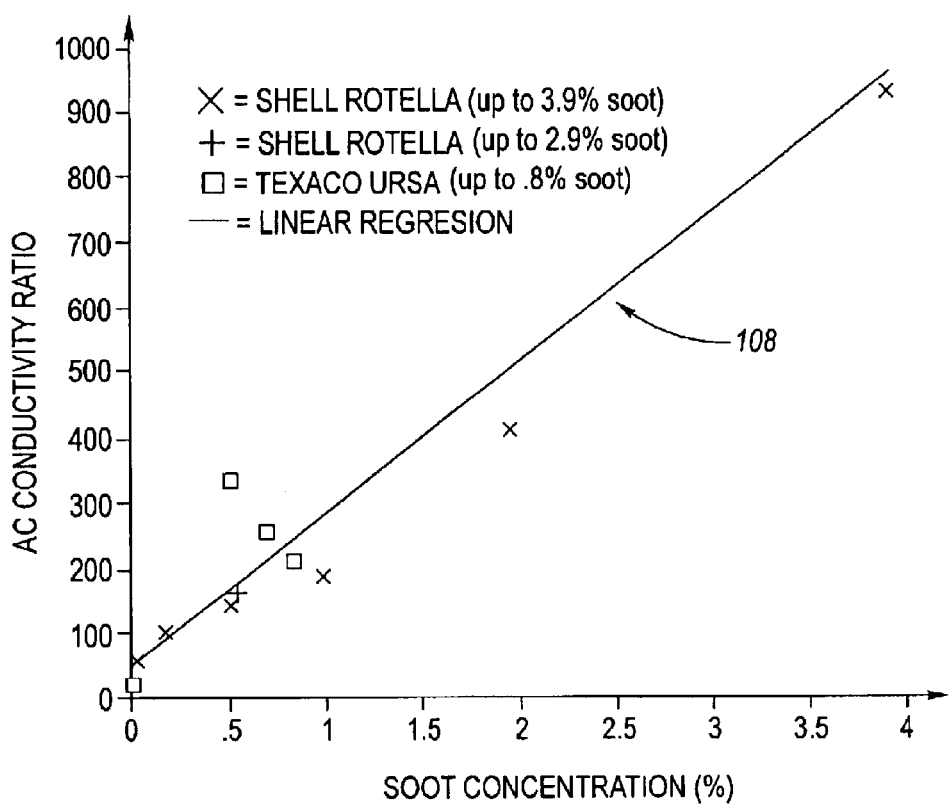
FIG. 7 is a plot of conductivity ratio versus soot concentration of the oils of FIGS. 3, 4, and 5.

FIG. 7 is a plot 108 of conductivity ratio versus soot concentration of the oils of FIGS. 3, 4, and 5 at room temperature wherein the conductivity ratio is the conductivity measured at 2 MHz divided by the conductivity measured at 20 Hz. The straight line is determined using linear regression and is represented by the relation Y=mX+b as: Y=234X+52, where Y represents the conductivity ratio and X represents the soot content in percent. FIG. 7 underscores that the conductivity ratio can be used to determine the soot content and that this method is brand independent thereby eliminating the need to reset the Diesel engine oil sensor after an oil change since the sensor would not need a memory of the initial properties of a particular brand of fresh oil.

FIG. 8 is a plot 110 of conductivity versus frequency of oil aged in a first vehicle while FIG. 9 is a plot 112 of conductivity versus frequency of another oil aged in a second vehicle. These plots 110, 112 were obtained from oil aged in actual Diesel engines and represent a true oil aging process to supplement the data obtained by mixing used and fresh oil.

FIG. 10 is a plot 114 of conductivity ratio versus soot concentration at a temperature of 20EC of the oils of FIGS. 8 and 9 as well as mixed oils while FIG. 11 is a plot 116 of conductivity ratio versus soot concentration at a temperature of 40EC of the oils of FIGS. 8 and 9 as well as mixed oils.

Figure 13:
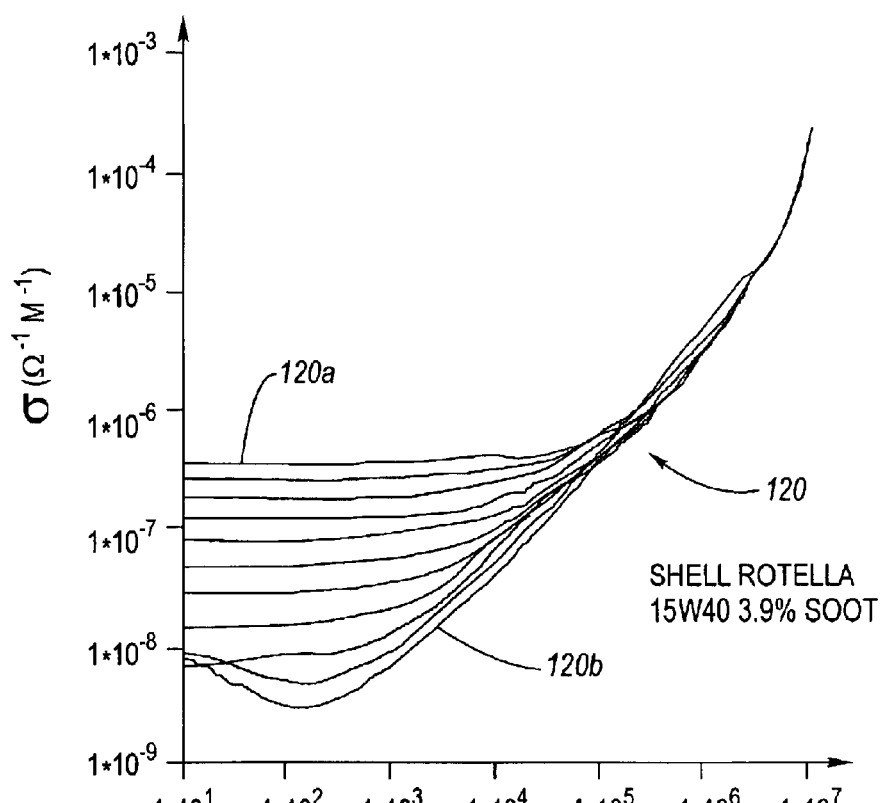
FIG. 13 is a plot of conductivity versus frequency of used oil of FIG. 12 at various temperatures.

C. to 0 degrees C. at plot 118b; while FIG. 13 is a plot 120 of conductivity versus frequency of used oil of FIG. 12 at various temperatures from 100 degrees C. for plot 120a through decrements of 10 degrees C. to 0 degrees C. at plot 120b. FIGS. 12 and 13 show that the conductivity has a large variation with temperature at low frequencies but has little or no variation with temperature at high frequencies.

Figure 14:
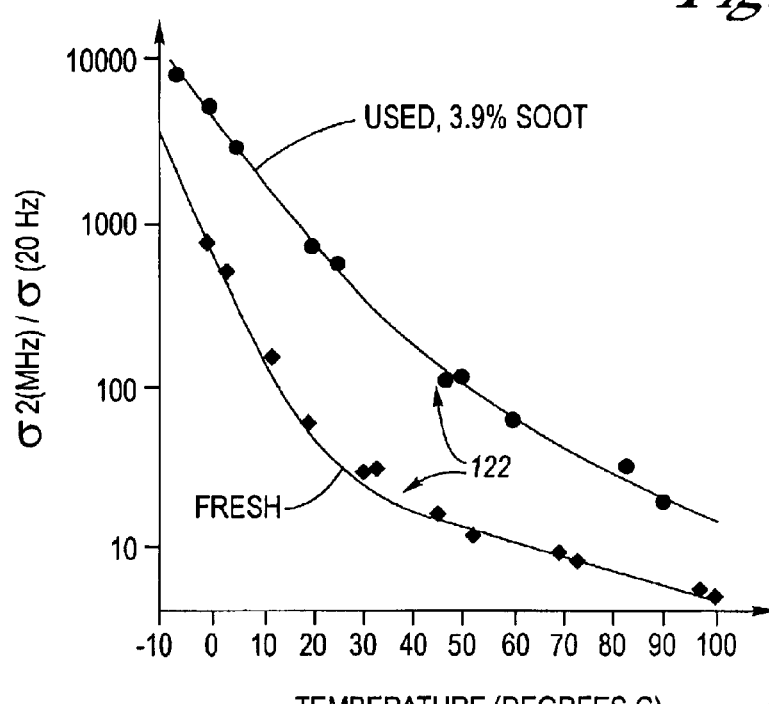
FIG. 14 is a plot of conductivity ratio versus temperature of the oils of FIGS. 12 and 13.

FIG. 14 is a plot 122 of conductivity ratio versus temperature of the oils of FIGS. 12 and 13 showing a non linear dependence due to the temperature dependence of the conductivity at the low frequency (20 Hz).

Figure 15:
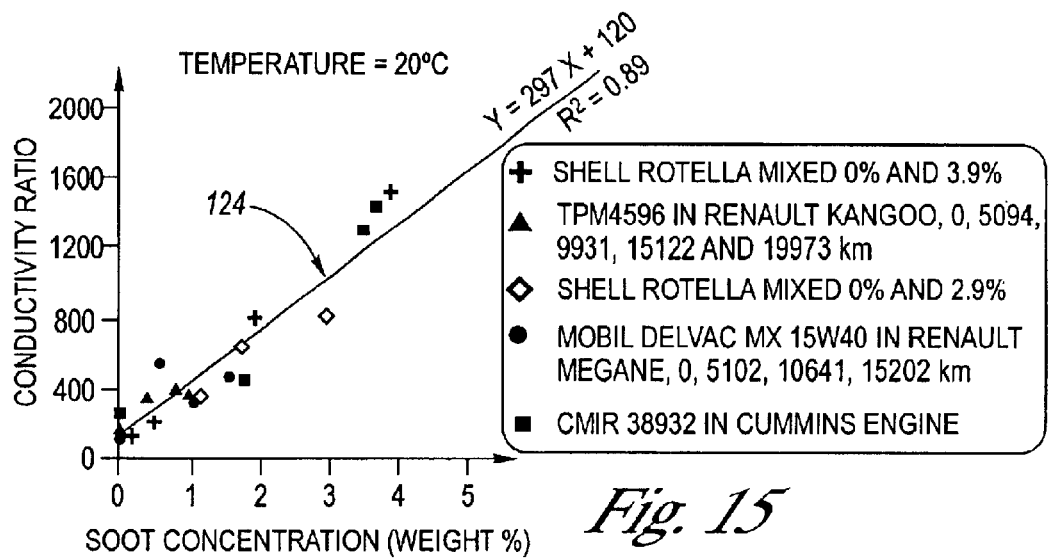
FIG. 15 is a plot of conductivity ratio versus soot concentration at 20 degrees C. for various brands of oil.
Figure 16:
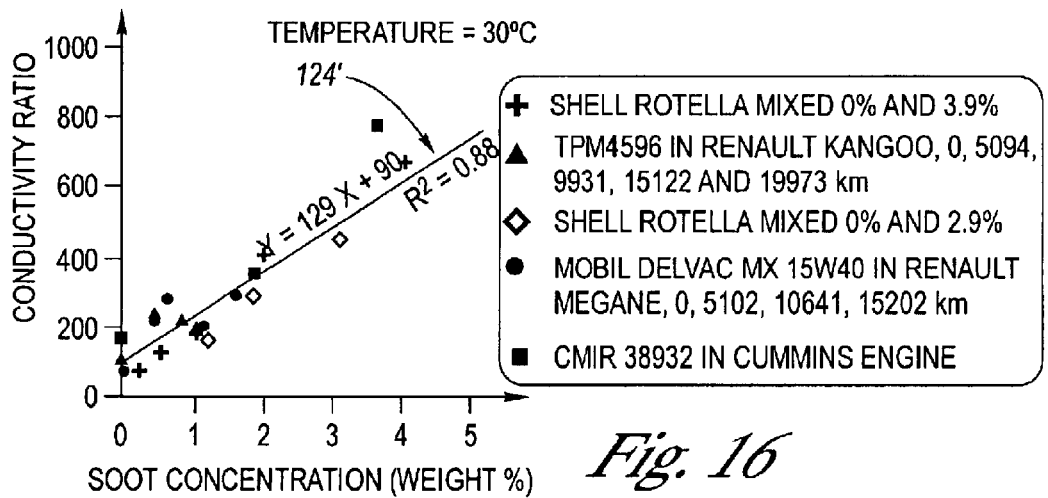
FIG. 16 is a plot of conductivity ratio versus soot concentration at 30 degrees C. for various brands of oil.
Figure 17:
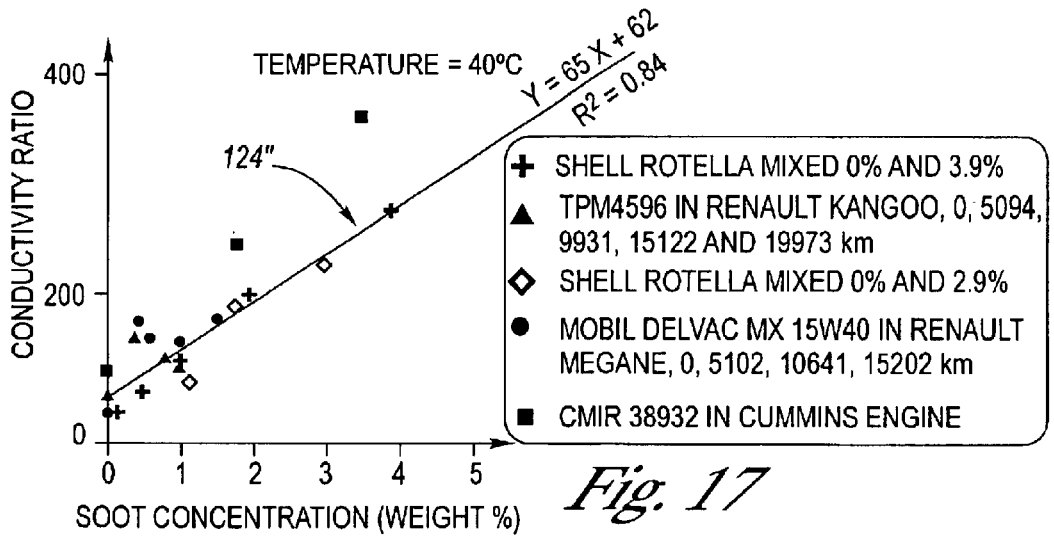
FIG. 17 is a plot of conductivity ratio versus soot concentration at 40 degrees C. for various brands of oil.

FIG. 15 is a plot 124 of conductivity ratio versus soot concentration at 20 degrees C. for various brands of oil, whereas FIG. 16 is a plot 124' of conductivity ratio versus soot concentration at 30 degrees C. for various brands of oil, and whereas FIG. 17 is a plot 124" of conductivity ratio versus soot concentration at 40 degrees C. for various brands of oil. FIGS. 15, 16, and 17 show the need to execute the conductivity ratio method at one selected temperature due to the temperature dependence of the conductivity at low frequencies and also shows that the lower the temperature the better the method.

Figure 18:
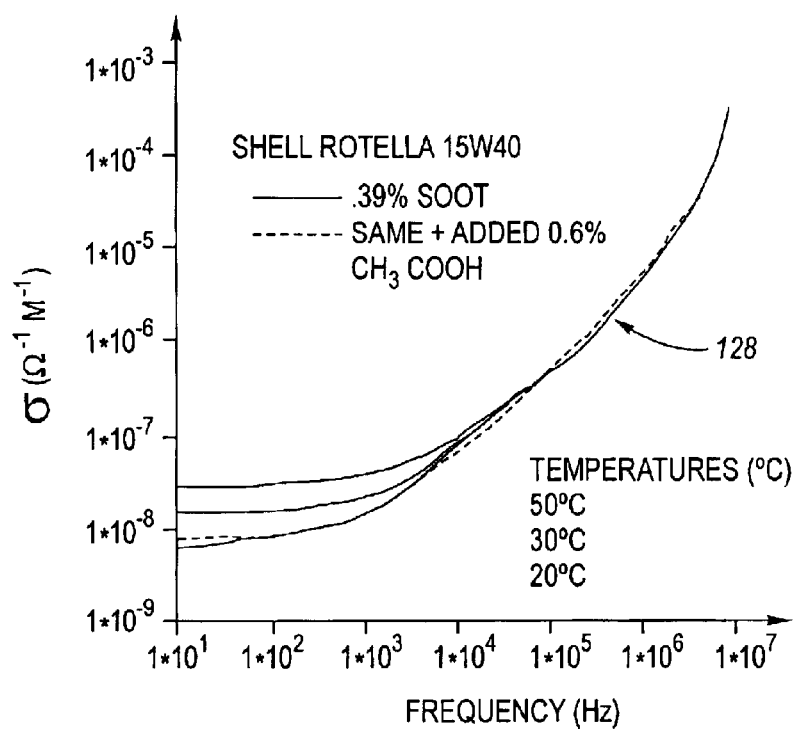
FIG. 18 is a plot of conductivity versus frequency of oil with acid and soot.
Figure 19:
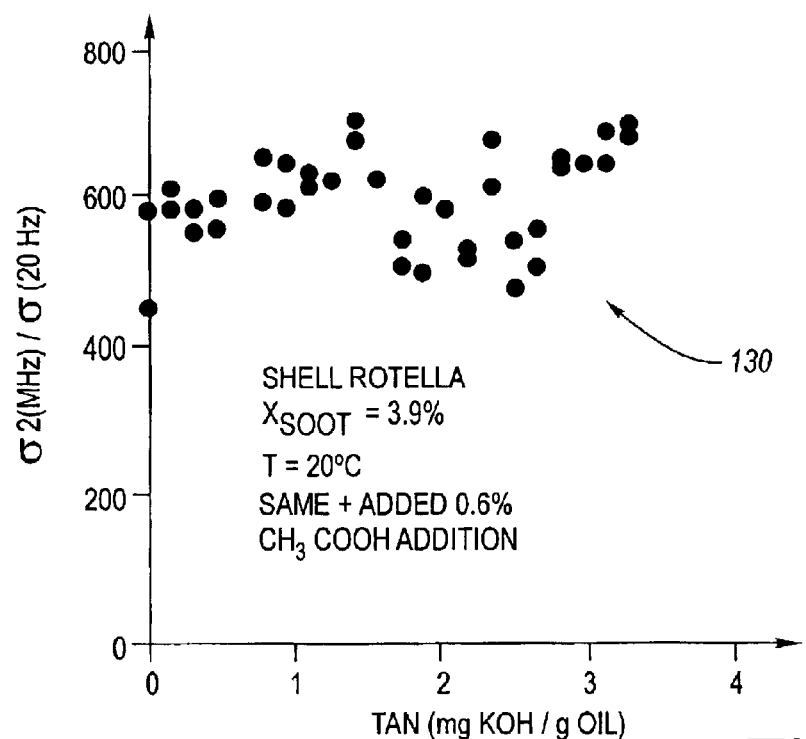
FIG. 19 is a plot of conductivity ratio versus total acid number of the oil with acid of FIG. 18.

FIG. 18 is a plot 128 of conductivity versus frequency of oil with soot to which acetic acid has been added whereas FIG. 19 is a plot 130 of conductivity ratio versus the resulting total acid number (TAN) of the oil with acid of FIG. 18 showing that there is no systematic effect of TAN on the conductivity ratio. However, even if the soot concentration and TAN were related, for instance if the soot particles were to absorb acid ions, then their combination would still be an indication of the condition of the Diesel engine oil and the conductivity ratio is still a good indicator of that condition.

Figure 20:
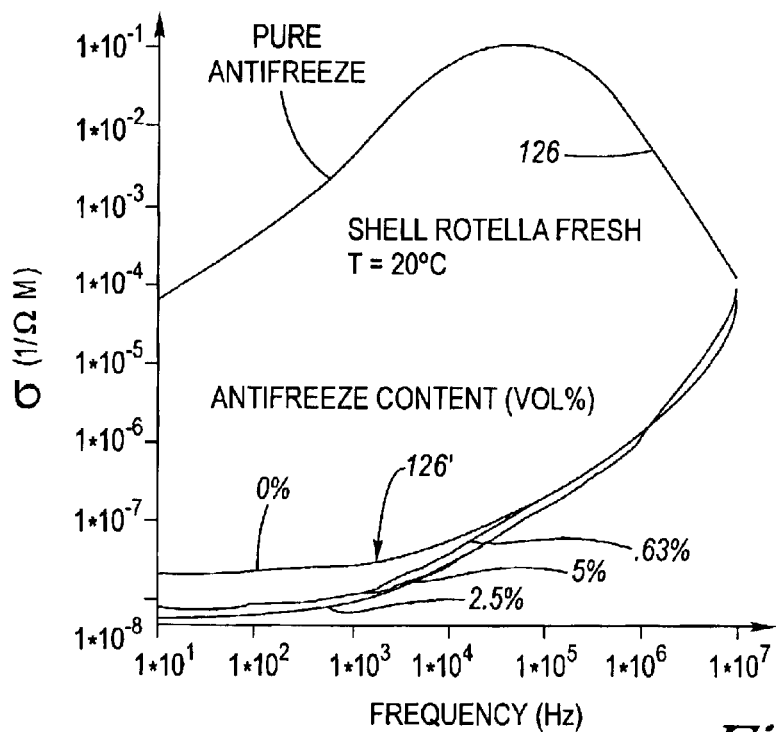
FIG. 20 is a plot of conductivity versus frequency of fresh oil with antifreeze.
Figure 21:
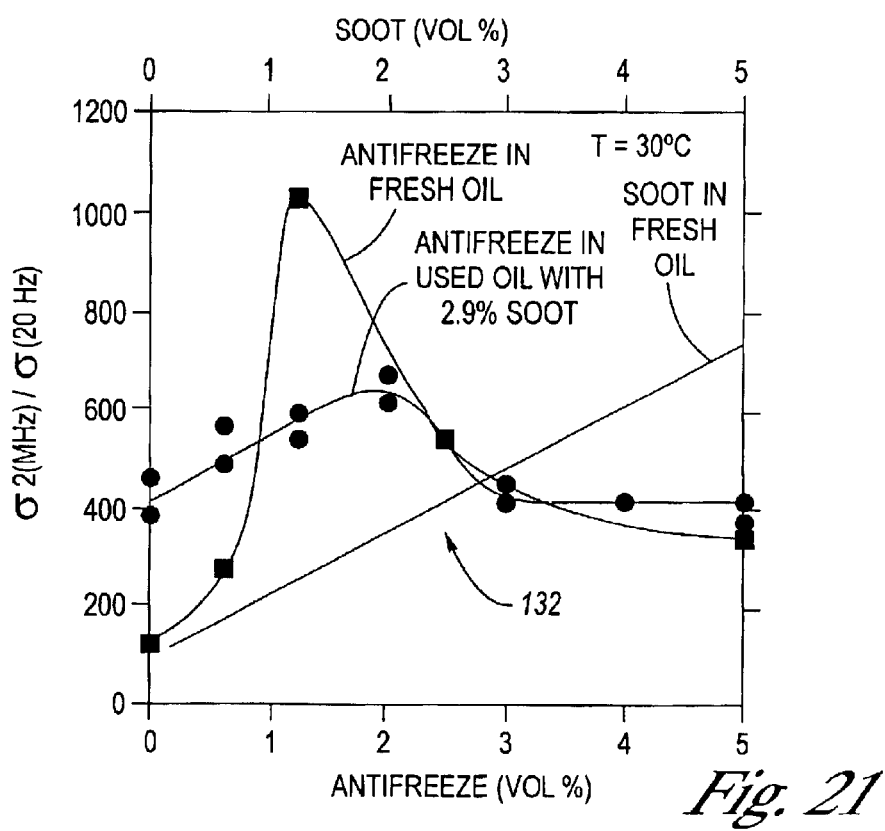
FIG. 21 is a plot of conductivity ratio versus percent antifreeze in fresh and used oil with soot.
Figure 22:
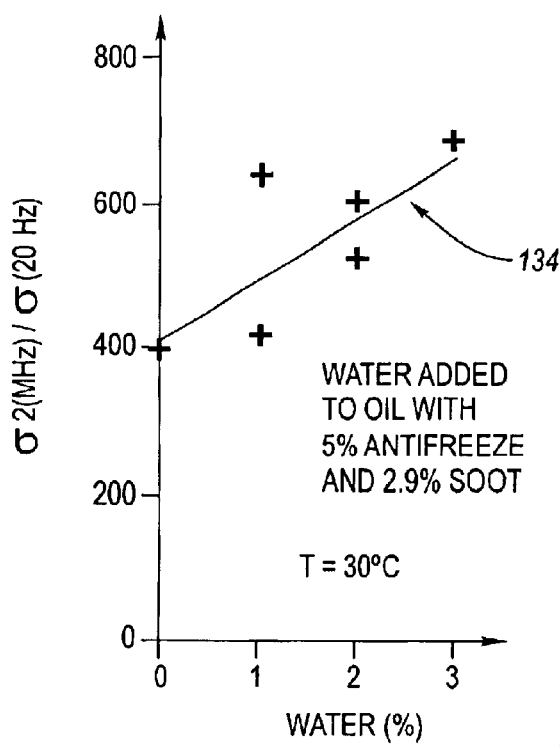
FIG. 22 is a plot of conductivity ratio versus percent water in oil with soot and antifreeze.

FIG. 20 shows plots 126, 126' of conductivity versus frequency for pure antifreeze (plot 126) and of fresh Shell Rotella oil to which various amounts of antifreeze have been added (Plot 126'); FIG. 21 is a plot 132 of conductivity ratio at 30 degrees C. versus percent antifreeze in fresh and used oil with soot; and FIG. 22 is a plot 134 of conductivity ratio versus percent water in oil with soot and antifreeze showing about the same sensitivity of the conductivity ratio to soot, antifreeze, and water. Whether the contaminant is soot, water or antifreeze, all three of these are indicative of oil condition. Since the conductivity ratio has a variance substantially similar for all three of these contaminants (antifreeze up to about 2% by volume) the conductivity ratio is a good indicator of oil condition.

Figure 23:
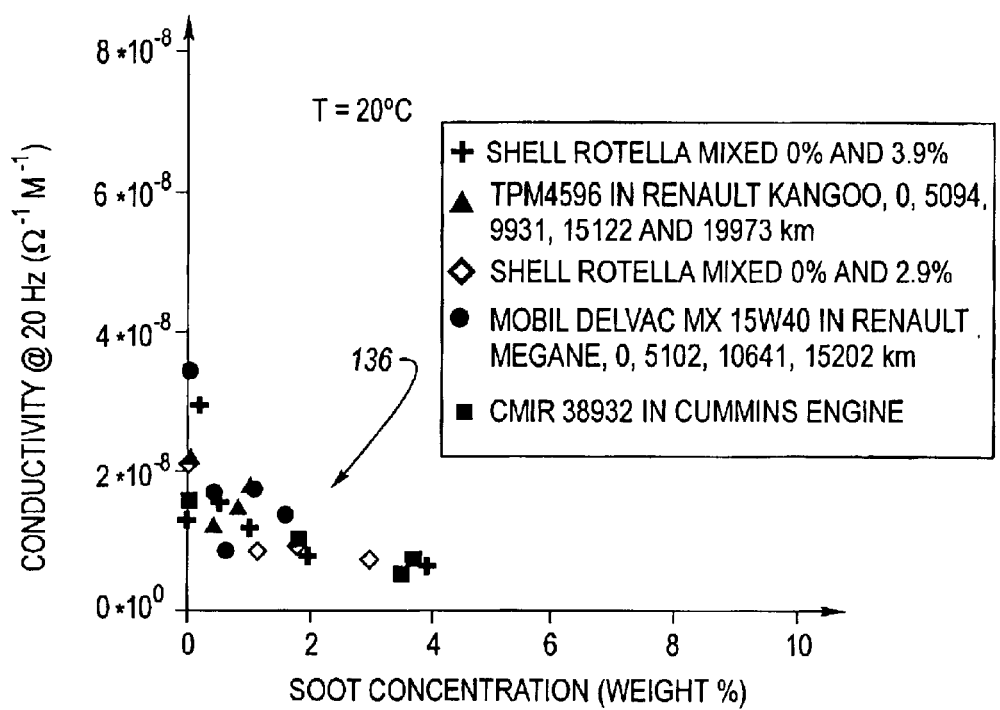
FIG. 23 is a plot of conductivity versus soot concentration at a low frequency for various brands of oil.
Figure 24:
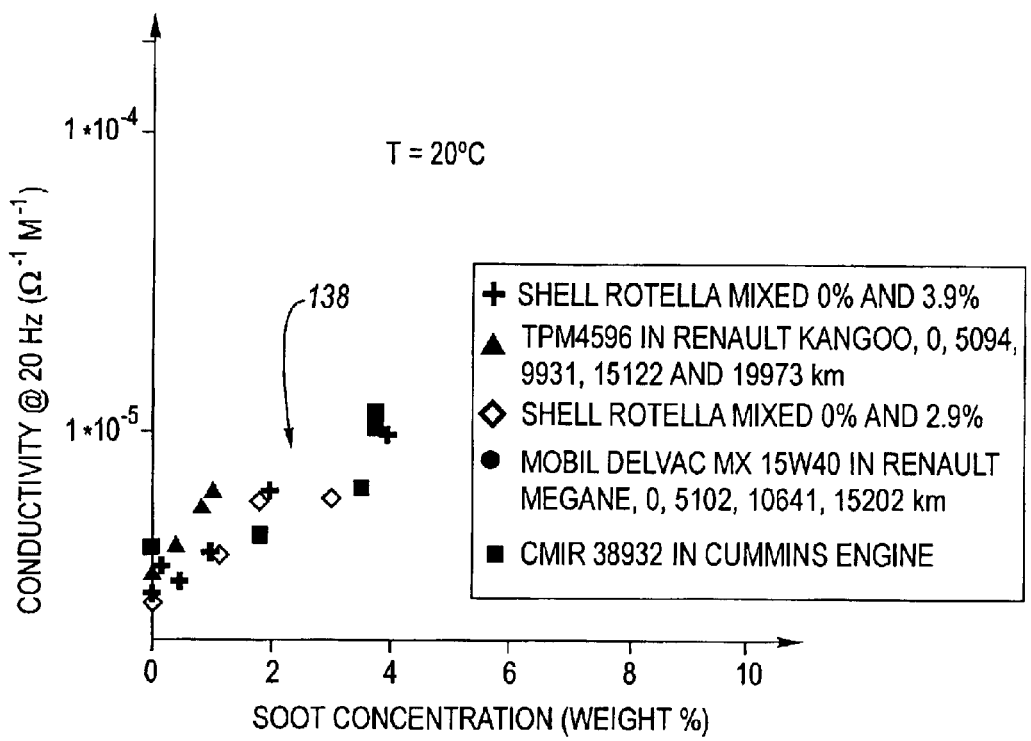
FIG. 24 is a plot of conductivity versus soot concentration at a high frequency for various brands of oil.

FIG. 23 is a plot 136 of conductivity versus soot concentration at a low frequency for various brands of oil, whereas FIG. 24 is a plot 138 of conductivity versus soot concentration at a high frequency for various brands of oil. While FIG. 24 shows a poor and non-linear correlation between soot concentration and low frequency conductivity, FIG. 24 is linear showing that the conductivity at a high frequency may be used to determine the soot concentration of Diesel engine oil.

Figure 25:
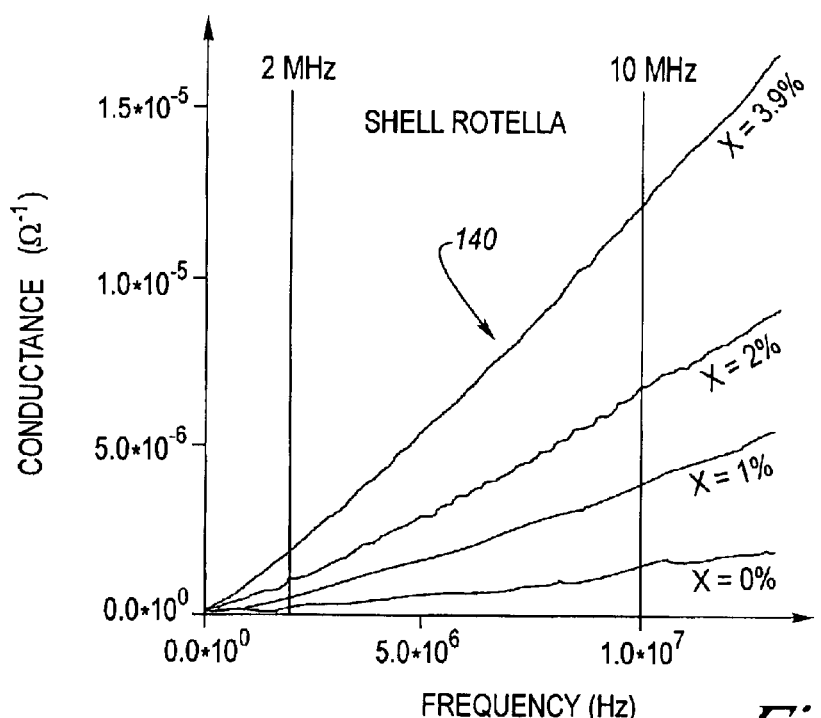
FIG. 25 is a plot of conductance versus frequency for oil with various soot concentrations.
Figure 26:
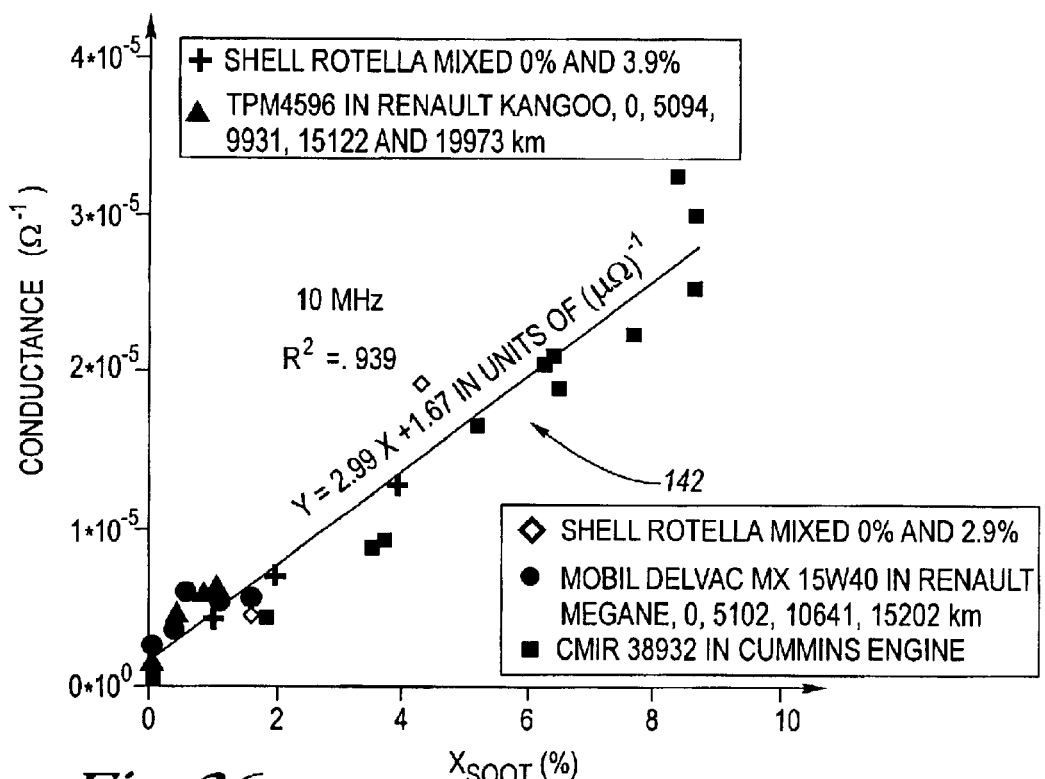
FIG. 26 is a plot of conductance versus soot concentration at 10 MHz for various brands of oil.

FIG. 25 is a plot 140 of the electrical conductance of the oil sensor 10 versus frequency for Diesel engine oil with various soot concentrations, whereas FIG. 26 is a plot 142 of conductance versus soot concentration at 10 MHz for various brands of Diesel engine oil. Since conductivity is directly proportional to conductance, FIGS. 25 and 26 show that the linearity of conductivity of Diesel engine oil at high frequencies versus soot concentration is brand independent, correlates with soot concentration, and, as previously mentioned, is temperature independent as well. The straight line is determined using linear regression and is represented by the relation Y=mX+b as: Y=2.99X+1.67 in units of $(\mu\Omega)^{-1}$, where Y represents the conductance and X represents the soot content in percent. Below about 2 MHz, all ionic species in the oil contribute to the conductivity. Above about 2 MHz, the conductivity is more dominated by the conductive soot particles due to the eddy currents induced in the soot by the high frequencies. The higher the frequency, the more the conductivity is dominated by soot. Hence, the higher the frequency the better the measurement is, up to the GHz range. However, there are economical limits. The wide availability of inexpensive commercial integrated circuits today implies a practical upper frequency of about 50 MHz.

Various electrical means or circuits may be designed or utilized to measure the conductivity of oil at low and high frequencies, such as, homodyne detection, utilizing a lock-in amplifier, Shering bridge methods, double RC bridge methods, phase-locked loops, resonant RLC circuits, and others, as are well known in the art.

Returning now to FIG. 2A, shown is a first example of an electrical circuit 50 to measure conductivity of oil at high frequencies utilizing a resonant RLC circuit. The Diesel oil sensor 10 is modeled as a capacitor 25 (see FIG. 1B) having capacitance C with a resistor R in parallel with the capacitor where 1/R represents the conductance of the physical configuration of the metal plates of the oil sensor 10 filled with Diesel engine oil to be measured, and C represents the capacitance of the physical configuration of the metal plates of the oil sensor 10 filled with the Diesel engine oil. The inductor L is chosen in accordance with the dimensions of the sensor 10 to provide circuit resonance at a frequency between, for example, 2 MHz and 3 MHz. Circuit element 52 is an analog to digital voltage (A/D) converter providing voltage $V_R$ as one input to microprocessor 56 while circuit element 54 is an (A/D) converter providing voltage $V_S$ as another input to the microprocessor. Circuit element 58 provides voltage, $V'_R$, at various frequencies depending upon the value of control voltage $V_0$ and may, for example, be a voltage to frequency converter. $V_R$ is a digital representation of $V'_R$. The power source for circuit element 58 is not shown. Circuit element 60 is such that the voltage $V'_S$ represents the current I through R at resonance, which occurs at high frequencies, and may be, for example, a resistor or a current to voltage converter, whose values and parameters are stored in microprocessor 56 whose input voltage $V_S$ is a digital representation of $V'_S$.

Circuit 50 operates as follows. For high frequencies, microprocessor 56 outputs various control voltages $V_0$ such that element 58 outputs a predetermined range of high frequencies, for example 2 MHz to 3 MHz, whereby voltage $V_S$ is monitored by the microprocessor until a maximum voltage is detected. At this maximum voltage, the circuit is in resonance whereby the inductive reactance of the inductor L cancels the capacitive reactance of the capacitance C of the oil sensor 10 and the circuit is purely resistive. $V'_R$ represents the voltage across R and element 60 whereas $V'_S$ is a representation of the current I through R. At resonance, the resonant frequency is $f_r=1/[2B\sqrt{(LC)}]$ and the current $I=(V_R-V_S)/R$, or equivalently $I=(V'_R-V'_S)/R$, is proportional to the resistance R only and independent of L and C. Hence, the conductivity or conductance can be determined by microprocessor 56 and is stored in memory wherein the conductance is $1/R=V_S/(V_R-V_S)$, or equivalently $1/R=V'_S/(V'_R-V'_S)$.

Microprocessor 56 has incorporated within it all parameters, constants, algorithms, and programs to effect the operation of the circuit 50 and the present invention utilizing the conductivity ratio and conductivity or conductance by techniques well known in the art.

FIG. 2B is a second example of an electrical circuit 50' to measure conductivity of oil at high frequencies utilizing a Schering Bridge, a technique well known in the art. The oil sensor 10 is modeled as a capacitor 25 (see FIG. 1B) having capacitance C with a resistor R in parallel with the capacitor where 1/R represents the conductance of the physical configuration of the metal plates of the oil sensor 10 filled with Diesel engine oil to be measured, and C represents the capacitance of the physical configuration of the metal plates of the oil sensor 10 filled with the Diesel engine oil. The oil sensor 10 comprises one arm of the Bridge. A second arm of the Bridge consists of capacitor $C_1$ while a third arm consists of resistor $R_1$. The fourth arm of the Bridge consists of a variable resistor $R_A$ in series with a variable capacitor $C_A$. The voltage $V_{AB}$ is the voltage between terminals A and B whereas the voltage $V_A$ is the voltage at terminal A measured with respect to ground and the voltage $V_B$ is the voltage at terminal B measured with respect to ground. $R_A$ could be a digitally controlled variable resistance and $C_A$ could be a varactor both controlled by microprocessor 56 by techniques well known in the art. Circuit element 52' is an analog to voltage (A/D) converter providing voltage $V'_B$ as one input to microprocessor 56 while circuit element 54' is an (A/D) converter providing voltage $V'_A$ as another input to the microprocessor. When $R_A$ and $C_A$ are varied and adjusted such that $V_A$ equals $V_B$ (equivalently, $V'_A=V'_B$) or $V_{AB}$ is zero, the bridge is balanced whereat $R=(C_A/C_1)R_1$.

Microprocessor 56 has incorporated within it all parameters, constants, algorithms, and programs to effect the operation of the circuit 50' and the present invention utilizing the conductivity ratio and conductivity or conductance by techniques well known in the art.

FIG. 2C is an example of an electrical circuit 50'' to measure the D.C. conductivity of oil utilizing a known constant current source I'. The oil sensor 10 is modeled as a capacitor 25 (see FIG. 1B) having capacitance C with a resistor R in parallel with the capacitor where 1/R represents the conductance of the physical configuration of the metal plates of the oil sensor 10 filled with Diesel engine oil to be measured, and C represents the capacitance of the physical configuration of the metal plates of the oil sensor 10 filled with the Diesel engine oil. Circuit element 52'' is an analog to digital voltage (A/D) converter providing voltage $V_{DC}$ as an input to microprocessor 56. $V_{DC}$ is a digital representation of analog voltage $V'_{DC}$. Voltage source $V_E$ represents an electrochemical voltage due to the electrochemical reactions of the Diesel oil within the oil sensor 10.

Circuit 50'' operates as follows for D.C. After switch S is closed for a predetermined time much longer than the RC time constant of the oil sensor, for example one-second, whereat the circuit is in a steady state condition, $V_{DC}$ is read by microprocessor 56 and, for example, is stored as $V_{DC}$ (closed). Thereafter, switch S is opened for a predetermined time much longer than the RC time constant of the oil sensor, for example one-second, whereat the circuit is in a steady state condition, $V_{DC}$ is read by microprocessor 56 and, for example, is stored as $V_{DC}$(open). The resistance R can be determined from R=[$V_{DC}$(closed)–$V_{DC}$(open)]/I'. The conductance is the reciprocal of the resistance (1/R) and the conductivity can be determined by the known parameters of the oil sensor and circuit. Microprocessor 56 has incorporated within it all parameters, constants, algorithms, and programs to effect the operation of the circuit 50'' and the present invention utilizing the conductivity ratio and conductivity or conductance by techniques well known in the art. The difference [$V_{DC}$(closed)–$V_{DC}$(open)] eliminates the electrochemical voltage $V_E$ thereby ensuring that the resistance R is properly determined.

The present invention indicates when Diesel engine oil has degraded by determining the amount of soot in Diesel engine oil either by use of the conductivity ratio or by the conductivity at high frequencies. The present invention enables a setpoint threshold for soot concentration to be chosen to indicate when the Diesel engine lubricating oil has degraded to an extent that it should be replaced with fresh Diesel engine oil. Furthermore, the present invention is independent of the brand of Diesel engine oil and is immune to the effects of adding fresh Diesel engine (lubricating) oil with different dielectric or electrical properties than that of the original oil. Thus, the present invention negates the necessity of the oil sensor to have a memory unit or microprocessor incorporated therein thereby simplifying the service of the Diesel engine by eliminating the need to reset the oil sensor after each oil change. The conductivity method of the present invention is also temperature independent.

In summary, the steps for carrying-out the method using a ratio methodology are as follows: First experimentally determined are a set of first oil condition constants, m and a set of second oil condition constants, b, wherein m and b are determined based upon a range of temperatures of oil. Now to obtain an oil condition indication of an oil being used in a selected Diesel engine, a first measurement is taken of a selected one of conductivity and conductance of the oil of the Diesel engine at a frequency above of about 2 MHz to thereby provide a first measured value. And, a second measurement is taken of the selected one of conductivity and conductance of the oil at a frequency below about 1 KHz to thereby provide a second measured value. Next, the temperature of the oil taken substantially contemporaneously with the second measured value measurement. Next, the microprocessor calculates a ratio, Y, of the first measured value with respect to the second measured value, and then calculates a contaminant concentration which is at least one of soot concentration, water concentration and antifreeze concentration, X, based upon the relation: Y=mX+b, wherein the values of m and b are selected from the sets of m and b already known from experiment which are appropriate for the measured temperature. Lastly, the microprocessor determines if the value of X has reached a predetermined threshold. For example, if X is not above (or optionally below) the threshold, then the microprocessor sends out an appropriate signal relating to the condition of the oil which may include an indication that the oil condition is acceptable; if X is above (or optionally at or above) the threshold, then the microprocessor sends out an appropriate signal relating to the condition of the oil which may include an indication that the oil condition is unacceptable.

In summary, the steps for carrying-out the method using the conductivity and conductance at high frequency methodology are as follows: First experimentally determined are a first oil condition constant, m, and a second oil condition constant, b. Now to obtain an oil condition indication of an oil being used in a selected Diesel engine, a measurement is taken of a selected one of conductivity and conductance of the oil of the Diesel engine at a frequency above of about 2 MHz to thereby provide a measured value, Y. Next, the microprocessor calculates a soot concentration, X, based upon the relation: Y=mX+b. Lastly, the microprocessor determines if the value of X has reached a predetermined threshold. For example, if X is not above (or optionally below) the threshold, then the microprocessor sends out an appropriate signal relating to the condition of the oil which may include an indication that the oil condition is acceptable; if X is above (or optionally at or above) the threshold, then the microprocessor sends out an appropriate signal relating to the condition of the oil which may include an indication that the oil condition is unacceptable.

Figure 27:
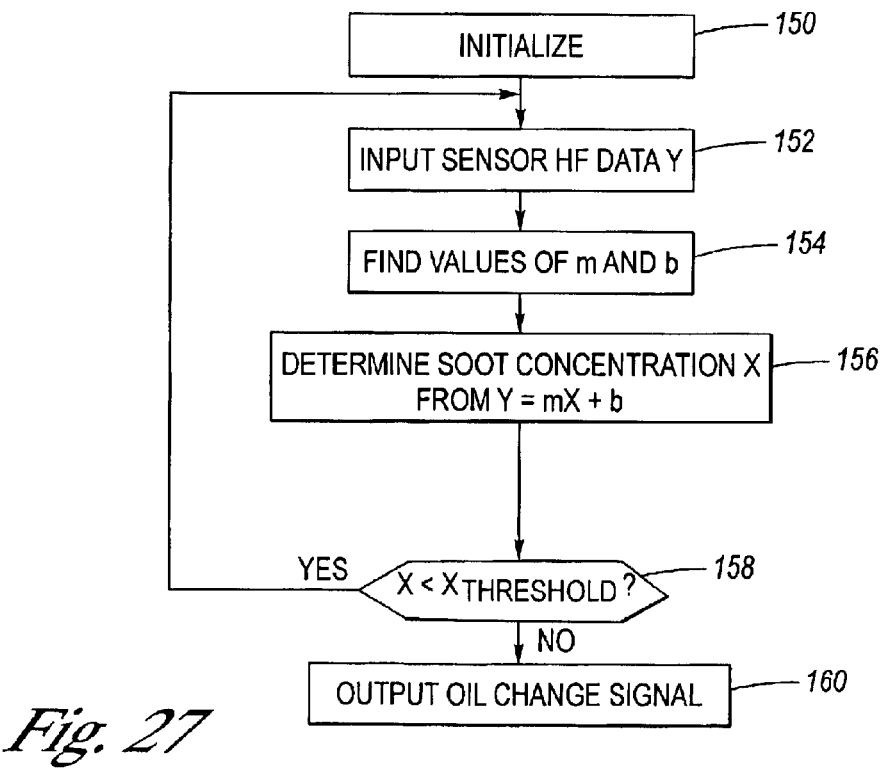
FIGS. 27 and 28 are examples of microprocessor flow charts for implementing the present invention.

FIG. 27 is an example of a microprocessor flow chart to implement the high frequency conductivity or conductance method according to the present invention. At block 150, microprocessor 56 is initialized with appropriate values and parameters and, if necessary, the high frequency circuit may be selected by microprocessor 56 through appropriate digitally controlled switches, the method being well known in the art. The sensor data is then input at block 152 whereat the value of Y is ascertained. At block 154, the appropriate values of m and b are found while the soot concentration X is determined at block 156 from Y=mX+b. Block 158 compares the value of x to the threshold value of the soot concentration $X_{THRESHOLD}$. At block 158, if the value of X#$X_{THRESHOLD}$, control passes to block 152 to repeat the process. Otherwise, an oil change signal is output at block 162.

Figure 28:
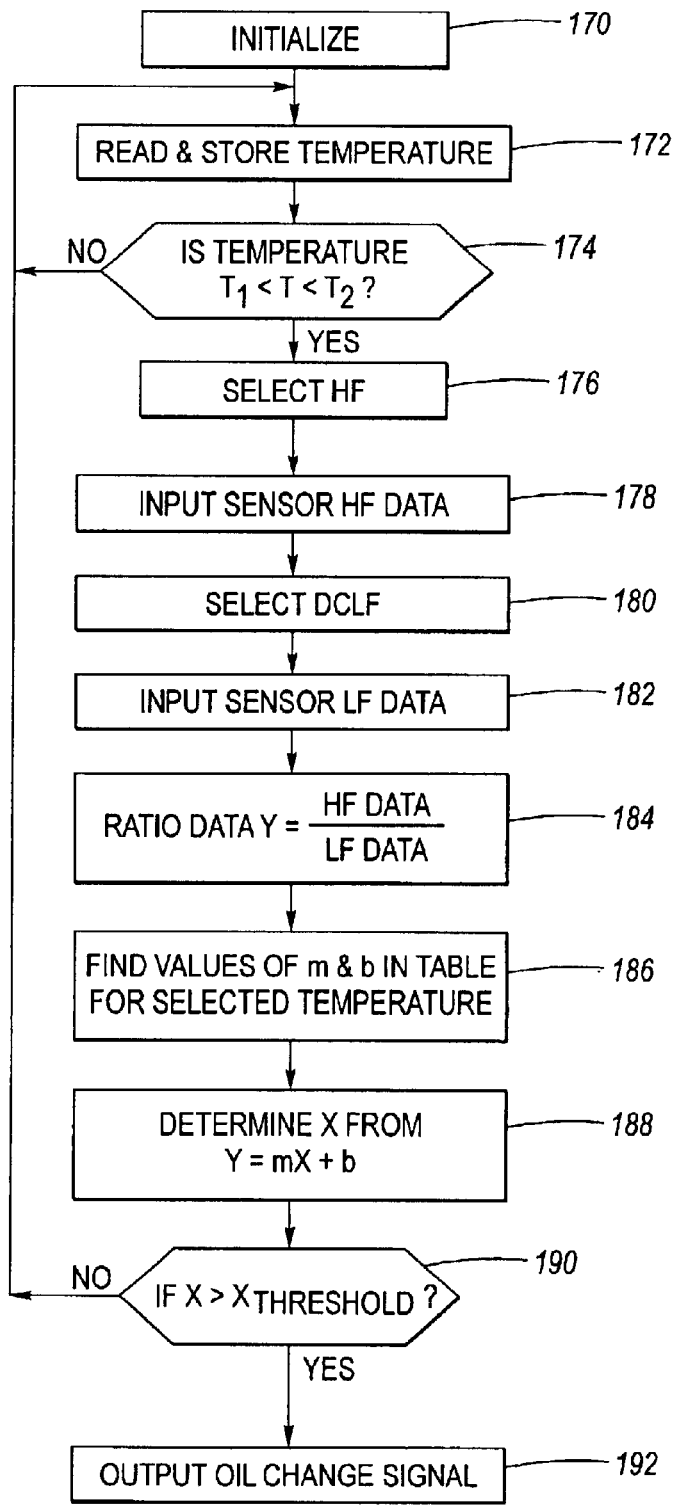

FIG. 28 is an example of a microprocessor flow chart to implement the conductivity ratio method according to the present invention. At block 170, microprocessor 56 is initialized with appropriate values and parameters. The temperature T from thermometric sensor 26 (see FIG. 1B) is read and stored at block 172. If the temperature T is not within a predetermined range ($T_1$<T<$T_2$), for example T is selected related to a normal operational temperature of a selected Diesel engine and the predetermined range is ∀ one degree C of T such that $T_1$=T−1° C. and $T_2$=T+1° C., block 174 passes control to block 172. Otherwise, block 174 passes control to block 176 whereat the high frequency circuit is selected. The high frequency circuit may be selected by microprocessor 56 through appropriate digitally controlled switches, the method being well known in the art.

The sensor data from the high frequency circuit is then input at block 178. The D.C. or low frequency circuit is selected next at block 180. The D.C. or low frequency circuit may be selected by microprocessor 56 through appropriate digitally controlled switches, the method being well known in the art. The sensor data from the D.C. or low frequency circuit is then input at block 182. At block 184, Y is determined from the ratio of the high frequency sensor data to the D.C. or low frequency sensor data. The values of m and b are found from the appropriate table for the selected temperature T at block 186 while X is determined at block 188 from Y=mX+b wherein X may be a representation of soot concentration, antifreeze concentration, or water concentration. Block 190 compares the value of x to the threshold value of the concentration $X_{THRESHOLD}$. If the value of $X>X_{THRESHOLD}$, an oil change signal is output at block 192. Otherwise, control passes to block 172 to repeat the process.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A method for determining engine lubricating oil condition of a Diesel engine, comprising the steps of:
   measuring a selected one of conductivity and conductance of lubricating oil of a Diesel engine at a frequency above of about 2 MHz to thereby provide a first measured value;
   measuring the selected one of conductivity and conductance of the oil at a frequency below about 1 KHz to thereby provide a second measured value;
   measuring a temperature of the oil taken substantially contemporaneously with said second step of measuring;
   determining a first oil condition constant, m;
   determining a second oil condition constant, b; wherein m and b are determined based upon a predetermined relationship with respect to the measured temperature;
   calculating a ratio, Y, of the first measured value with respect to the second measured value;
   calculating a contaminant concentration, X, based upon a relation:

$Y=mX+b$; and determining whether X has reached a predetermined threshold;
   wherein if X is below the threshold, then the engine oil condition has a first condition; and if X is at least one of at the threshold or above the threshold, then the engine oil condition has a second condition.

2. The method of claim 1, further comprising generating an indication which is indicative of the engine oil having the second condition.

3. The method of claim 1, wherein said first measured value is measured at a selected frequency substantially between about 2 MHz and about 50 MHz.

4. The method of claim 3, further comprising generating an indication which is indicative of the engine oil having the second condition.

5. The method of claim 1, wherein said step of calculating calculates at least one of soot concentration of the oil, water concentration of the oil, and antifreeze concentration of the oil below about 2 percent by volume.

6. The method of claim 5, wherein said first measured value is measured at a selected frequency substantially between about 2 MHz and about 50 MHz.

7. The method of claim 6, further comprising generating an indication which is indicative of the engine oil having the second condition.

8. A method for determining engine lubricating oil condition of a Diesel engine, comprising the steps of:
   measuring a selected one of conductivity and conductance of lubricating oil of a Diesel engine at a frequency above of about 2 MHz to thereby provide a first measured value;
   measuring the selected one of conductivity and conductance of the oil at a frequency below about 1 KHz to thereby provide a second measured value;
   measuring a temperature of the oil taken substantially contemporaneously with said second step of measuring;
   determining a first oil condition constant, m;
   determining a second oil condition constant, b; wherein m and b are determined based upon a predetermined relationship with respect to the measured temperature;
   calculating a ratio, Y, of the first measured value with respect to the second measured value;
   calculating a soot concentration, X, based upon a relation:

$Y=mX+b$; and determining whether X has reached a predetermined threshold;
   wherein if X is below the threshold, then the engine oil condition has a first condition; and if X is at least one of at the threshold or above the threshold, then the engine oil condition has a second condition.

9. The method of claim 8, further comprising generating an indication which is indicative of the engine oil having the second condition.

10. The method of claim 8, wherein said first measured value is measured at a selected frequency substantially between about 2 MHz and about 50 MHz.

11. The method of claim 10, further comprising generating an indication which is indicative of the engine oil having the second condition.

12. A method for determining engine lubricating oil condition of a Diesel engine, comprising the steps of:
    measuring a selected one of conductivity and conductance of lubricating oil of a Diesel engine at a frequency above of about 2 MHz to thereby provide a measured value, Y;
    determining a first oil condition constant, m;
    determining a second oil condition constant, b;
    calculating a soot concentration, X, based upon a relation:

$Y=mX+b$; and determining whether X has reached a predetermined threshold;
    wherein if X is below the threshold, then the engine oil condition has a first condition; and if X is at least one of at the threshold or above the threshold, then the engine oil condition has a second condition.

13. The method of claim 12, further comprising generating an indication which is indicative of the engine oil having the second condition.

14. The method of claim 12, wherein said first measured value is measured at a selected frequency substantially between about 2 MHz and about 50 MHz.

15. The method of claim 14, further comprising generating an indication which is indicative of the engine oil having the second condition.

* * * * *